United States Patent [19]

Pasternak et al.

[11] Patent Number: 4,960,519

[45] Date of Patent: Oct. 2, 1990

[54] MEMBRANE PROCESS FOR SEPARATION OF ORGANIC LIQUIDS

[75] Inventors: Mordechai Pasternak, Spring Valley; Craig R. Bartels, Wappingers Falls; John Reale, Jr., Wappingers Falls; Vatsal M. Shah, Wappingers Falls, all of N.Y.

[73] Assignee: Texaco Inc., White Plains, N.Y.

[21] Appl. No.: 421,878

[22] Filed: Oct. 16, 1989

[51] Int. Cl.$^5$ ............................................. B01D 61/36
[52] U.S. Cl. ........................................ 210/640; 55/16; 55/158; 210/500.35
[58] Field of Search ...................... 210/500.3, 636, 640, 210/634, 637, 644, 649–654, 500.1, 500.21, 500.27, 500.35; 55/16, 158

[56] References Cited

U.S. PATENT DOCUMENTS 4,082,659 4/1978 Heinze et al. .................... 210/636
4,188,418 2/1980 Livingston ...................... 210/500.3

Primary Examiner—Frank Sever
Attorney, Agent, or Firm—Robert A. Kulason; O'Loughlin; Carl G. Seutter

[57] ABSTRACT

A mixture of alcohol, such as methanol, and organic oxygenate, such as dimethyl carbonate, is treated to recover product of decreased methanol content by pervaporation across a composite membrane of a polyvinyl alcohol and a polyacrylic acid on a polyacrylonitrile support layer.

6 Claims, No Drawings

MEMBRANE PROCESS FOR SEPARATION OF ORGANIC LIQUIDS

RELATED APPLICATIONS

Application Ser. No. 07/214,987 filed July 5, 1888 entitled Solvent Dewaxing Process of Mordechai Pasternak, Craig R. Bartels, and John Reale, Jr. now pending.

Application Ser. No. 07/166,575 filed Mar. 10, 1988 entitled Separation of Organic Liquids of Mordechai Pasternak, Craig R. Bartels, and John Reale, Jr.—issued Jan. 17, 1989 as U.S. Pat. No. 4,798,674.

Application Ser. No. 07/222,871 filed July 22, 1988 entitled Separation of Organic Liquids of Mordechai Pasternak, Craig R. Bartels, and John Reale, Jr. U.S. Pat. No. 4,877,529.

FIELD OF THE INVENTION

This invention relates to the separation of organic liquids. More particularly it relates to treatment of reaction mixtures containing products such as methyl t-butyl ether or dimethyl carbonate to remove methanol therefrom.

BACKGROUND OF THE INVENTION

As is well known to those skilled in the art, it is possible to separate mixtures of liquids by various techniques including adsorption or distillation. These conventional processes, particularly distillation, are however characterized by high capital cost. In the case of distillation for example, the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the charge components form an azeotrope, additional problems may be present which for example, could require that separation be effected in a series of steps (e.g. as in two towers) or by addition of extraneous materials to the system.

There are also comparable problems which are encountered in adsorption systems.

It has been found to be possible to utilize membrane systems to separate mixtures of liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
|---|---|
| Polyvinyl alcohol containing glycerine | Kuraray Co. Japanese Patent 81/193495 (1981) JP 58/g5522A2 (1983) |
| Nafion brand of perfluorosulfonic acid | Cabasso and Liu J. Memb. Sci. 24, 101 (1985) |
| Sulfonated polyethylene | Cabasso, Korngold & Liu, J. Pol. Sci.: Letters, 23, 57 (1985) |
| Fluorinated Polyether or Carboxylic Acid Fluorides | U.S. Pat. No. 4,526,948 to DuPont as assignee of Resnickto |
| Selemion AMV blend of Asahi Glass cross-linked styrene butadiene (with quaternary ammonium residues on a polyvinyl chloride backing | Wentzlaff Boddeker & Hattanbach J. Memb. Sci. 22,333 (1985) |
| Cellulose triacetate | Wentzlaff, Boddeker & Hattanback, J. Memb. Sci. 22, 333 (1985) |
| Polyacrylontrile or Polytetrafluoroethylene grafted with N-vinyl pyrrolidone | Neel, Aptel & Clement Desalination 53, 297 (1985) |
| Cellulose Acetate and others | Proc. of Int. Mem. Conf. Sept., 1986 Ottawa, p 229 |
| Crosslinked Polyvinyl Alcohol | Eur. Patent 0 096 339 to GFT as assignee of Bruschke |
| Poly(maleimide-acrylonitrile) | Yoshikawa et al J. Pol. Sci. 22, 2159 (1984) |
| Dextrine-isophoronediisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European patent No. 0 096 339 A2 of GFT as assignee of Bruschke—published 21 December 1983.

European Patent No. 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of crosslinked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses*, Gordon and Breach Science Publishers, New York (1970) or C. A. Finch, *Polyvinyl Alcohol, Properties and Applications*, John Wiley and Sons, New York (1973).

It is an object of this invention to provide a separation process. Other objects will be apparent to those skilled in the art.

STATEMENT OF THE INVENTION

In accordance with certain of its aspects, this invention is directed to a method of treating a charge composition containing (i) an alcohol having less than three carbon atoms and (ii) an oxygenate selected from the group consisting of organic ethers, aldehydes, ketones, and esters which comprises maintaining a non-porous membrane separating layer of a blend of a polyvinyl alcohol and a polyacrylic acid on a polyacrylonitrile support layer;

maintaining a pressure drop across said non-porous separating layer;

passing a charge composition containing (i) an alcohol having less than three carbon atoms and (ii) an oxygenate selected from the group consisting of organic ethers, aldehydes, ketones, and esters into contact with the high pressure side of said non-porous separating layer whereby at least a portion of said alcohol in said charge composition and a lesser portion of oxygenate pass by pervaporation through said non-porous separating layer as a lean mixture containing more alcohol and less oxygenate than are present in said charge composition and said charge composition is converted to a rich liquid containing less alcohol and more oxygenate than are present in said charge composition;

recovering as permeate from the low pressure side of said non-porous separating layer said lean mixture containing more alcohol and less oxygenate than are present in said charge composition, said lean mixture being recovered in vapor phase at a pressure below the vapor pressure thereof; and recovering as retentate from the high pressure side of said non-porous separating layer said rich liquid containing a lower alcohol content and a higher oxygenate content than are present in said charge composition.

DESCRIPTION OF THE INVENTION

The composite structure which may be used in practice of this invention includes a multi-layer assembly which in the preferred embodiment preferably may include a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, woven fibrous polyester.

One typical woven polyester carrier layer may be formulated of woven, bonded strands.

THE POROUS SUPPORT LAYER

The porous support layer which may be used in practice of this invention is preferably formed of a sheet or membrane of polyacrylonitrile polymer. Typically the polyacrylonitrile may be of thickness of 40–80 microns, say 50 microns and of molecular weight $\overline{M}_n$ of 5,000–100,000, preferably 20,000–60,000, more preferably 20,000–70,000 say 40,000. The polyacrylonitrile is preferably characterized by a pore size of less than about 500 Å and typically about 200 Å. This corresponds to a molecular weight cut-off of less than about 50,000, typically about 40,000.

THE SEPARATING LAYER

The separating layer which permits attainment of the separation in accordance with this invention includes a non-porous film of a blend of a polyvinyl alcohol and a polyacrylic acid.

In accordance with certain of its aspects, when the separating layer is a blend or a mixture of vinyl alcohol polymer and a polymer of an acrylic acid such as acrylic acids or methacrylic acid, the charge from which the separating membrane is to be prepared may be an aqueous solution containing a vinyl alcohol polymer and a polymer of an acrylic acid. Typically the aqueous solution may contain 5–10 w %, say 7 w % of polyvinyl alcohol of molecular weight $\overline{M}_n$ of 20,000–200,000, more preferably 96,000–115,000 say 115,000 and 5–10 w %, say 7 w % of polyacrylic acid of molecular weight $\overline{M}_n$ of 90,000–300,000, more preferably 90,000–250,000 say 250,000. The weight ratio of vinyl alcohol polymer to acrylic acid polymer may be 0.1–10:1, say 1:1.

The composite membrane, prepared from the blend of a polyvinyl alcohol and a polyacrylic acid, may be cured in an oven at 100° C.–175° C., say 125° C. for 1–30 minutes, say 8 minutes to yield a film having a thickness of 1–10 microns, say 2 microns.

It is possible that during curing, the polyvinyl alcohol and the polyacrylic acid may crosslink or otherwise react to form ester linkages.

THE PERVAPORATION MEMBRANE

It is a feature of this invention that the composite membrane used in the process of this invention may typically comprise (i) an optional carrier layer, characterized by porosity and mechanical strength, for supporting a porous support layer and a separating layer, (ii) a preferred polyacrylonitrile porous support layer of molecular weight of 5,000–100,000, of thickness of 10–80 microns, and of molecular weight $\overline{M}_n$ cut off of 25,000–50,000, and (iii) as a non-porous separating layer a blend of a polyvinyl alcohol and a polyacrylic acid.

The membranes of this invention may be utilized in various configurations. It is, for example, possible to utilize the composite in a plate-and-frame configuration in which separating layers may be mounted on the porous support layer with the carrier layer.

It is possible to utilize a spiral wound module (in the case of a supported membrane) which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There is then placed on one face of the bag-like unit, adjacent to the separating layer, and coterminous therewith, a feed channel sheet—typically formed of a plastic foraminous net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the perforations of the conduit; and the bag-like unit is wrapped around the conduit to form a spiral wound configuration. It will be apparent that, although only one feed channel is present, the single feed channel in the wound assembly will be adjacent to two faces of the membrane layer. The spiral wound configuration may be formed by wrapping the assembly around the conduit a plurality of times to form a readily handlable unit. The unit is fitted within a shell (in manner comparable to a shell-and-tube heat exchanger) provided with an inlet at one end and an outlet at the other. A baffle-like seal between the inner surface of the shell and the outer surface of the spiral-wound unit prevents fluid from bypassing the operative membrane system and insures that fluid enters the membrane system principally at one end. The permeate passes from the feed channel, into contact with the separating layer and thence therethrough, into the permeate channel and thence therealong to and through the perforations in the conduit through which it is withdrawn as net permeate.

In the case of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system.

In another embodiment, it is possible to utilize the system of this invention as a tubular or hollow fibre. In this embodiment, the porous support (polyacrylonitrile) layer may be extruded or spun as a fine tube with a wall thickness of typically 0.001–0.1 mm. The extruded tubes are passed through a bath of polyvinyl alcohol/polyacrylic acid which is cured in situ on the tubes. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid may be admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer.

PERVAPORATION

It is a feature of the non-porous separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 2 mm. Hg.

For general background on pervaporation, note U.S. Pat. Nos. 4,277,344; 4,039,440; 3,926,798; 3,959,247; 4,035,291; etc.

In practice of the pervaporation process of this invention, the charge solution at 40° C.–120° C., say 70° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 1–20 preferably 1–10, say 2 mm. Hg.

The permeate which passes through the membrane includes alcohol and a small proportion of the other components of the charge liquid. Typically, the permeate contains 90–99.9 w %, say 99 w % alcohol. Permeate is recovered in vapor phase.

Pervaporation may typically be carried out at a flux of about 0.04–2.2, say 0.13 kilograms per square meter per hour (kmh). Typically, the units may have Selectivity (measured in terms of w % alcohol in the permeate) of 96–99.9, say 99.3%. In terms of e.g. w % DMC in the permeate, the Selectivity may be 0.7–7.4, say 0.76 w %.

The Separation Factor S or Sep which represents the ability of the membrane to separate is calculated as follows:

$$S = \frac{\left(\frac{X_n}{X_m}\right)_p}{\left(\frac{X_n}{X_m}\right)_f}$$

wherein $X_n$ and $X_m$ are the weight fractions of alcohol and oxygenate components respectively in the permeate (p) and the feed (f). A system showing no separation at all would have a Separation Factor of 1; and a system showing perfect 100% separation would have a Separation Factor of infinity. The process of the instant invention may commonly have a Separation Factor of about 4–60, typically 20–60, say about 50.

It is a feature of this invention that the novel membrane may be particularly useful in pervaporation processes for concentrating a charge composition containing (i) an alcohol and (ii) oxygenate selected from the group consisting of organic ethers, aldehydes, ketones, and esters.

The oxygenate may be:

(i) an organic ether such as dimethyl ether, diethyl ether, di-n-propyl ether, di-n-butyl ether, methyl t-butyl ether, ethyl t-butyl ether, methyl t-amyl ether, ethyl t-amyl ether, etc.;

(ii) an aldehyde such as acetaldehyde, propionaldehyde, butyraldehyde, benzaldehyde, etc.;

(iii) a ketone such as acetone, methyl ethyl ketone, diethyl ketone, etc.; or (iv) an ester such as methyl acetate, methyl propionate, methyl butyrate, methyl benzoate, dimethyl carbonate, diethyl carbonate, etc.

The alcohol may typically be methanol or ethanol.

It will be obvious to those skilled in the art that the process of this invention may find particular use when the charge mixture to be treated is a reaction product wherein one of the components to be separated is unreacted charge component. A typical such charge mixture is the charge solution attained from the reaction of methanol, oxygen, and carbon monoxide wherein the mixture may contain unreacted methanol and product dimethyl carbonate (DMC). Another illustrative charge mixture is that attained from the reaction of methanol and isobutene wherein the reaction mixture may contain methanol and methyl t-butyl ether (MTBE).

These charge mixtures may have been subjected to preliminary separation, e.g. distillation, to yield, for example, an azeotrope of methanol and dimethyl carbonate.

TABLE

| Example | PVA/PAA Ratio | Membrane PVA/PAA (MW × 1000) | Curing T° C. | Feed % DMC | Performance Permeate % DMC | Sep | Flux |
|---|---|---|---|---|---|---|---|
| I | 50/50 | 115/250 | 150 | 27.4 | 0.7 | 53.5 | 0.13 |
| II | 70/30 | 115/250 | 150 | 29.3 | 1.9 | 21.4 | 0.12 |
| III | 30/70 | 115/250 | 150 | 27.4 | 1.3 | 28.7 | 0.04 |
| I | 50/50 | 115/250 | 150 | 27.4 | 0.7 | 53.5 | 0.13 |
| IV | 50/50 | 115/250 | 140 | 27.3 | 1.8 | 20.5 | 0.03 |
| V | 50/50 | 115/250 | 125 | 27.3 | 1.5 | 24.7 | 0.03 |
| VI | 50/50 | 115/250 | 110 | 27.3 | 2.4 | 15.3 | 0.04 |
| VII | 50/50 | 96/250 | 150 | 26.6 | 7.4 | 4.5 | 1.62 |
| VIII | 50/50 | 96/90 | 150 | 26.6 | 6.8 | 5.0 | 2.26 |
| IX | 50/50 | 115/90 | 150 | 26.6 | 1.5 | 23.8 | 0.12 |
| I | 50/50 | 115/250 | 150 | 27.4 | 0.7 | 53.5 | 0.13 |

Other charge mixtures may include (i) methyl acetate-methanol, (ii) ethyl acetate-ethanol, etc.

DESCRIPTION OF SPECIFIC EMBODIMENTS

Practice of the process of this invention will be apparent to those skilled in the art from inspection of the following examples wherein, as elsewhere in this specification, all parts are parts by weight unless otherwise stated.

EXAMPLE I

In this example, which represents the best mode presently known of carrying out the process of this invention, the porous support layer is the DUY-L brand of polyacrylonitrile membrane mounted on an inert carrier layer. The porous support layer has a molecular weight cut-off of 40,000. The separating layer is formed from an aqueous solution containing 10 g of 7 w % polyvinyl alcohol PVA (M.W. of 115,000) and 10 g of 7 w % polyacrylic acid PAA (M.W. of 250,000). This 50/50 mixture is stirred until homogeneous and spread onto the polyacrylonitrile microporous support to form a film 4 mils thick. The assembly is cured in an oven for 3 minutes at 150° C.

The membrane is evaluated in a pervaporization cell to which the charge at 70° C. is a mixture containing 27.4 w % dimethyl carbonate (DMC) and 72.6 w % methanol.

The concentration of DMC in the Permeate is only 0.7 w %. The Separation Factor is 53.5 and the Flux is 0.13 kmh.

EXAMPLES II-III

In this series of examples the conditions of Example I are duplicated except that in Example II, the weight ratio of PVA/PAA is 70/30 and in Example III, it is 30/70.

EXAMPLES IV-VI

In this series of examples, the conditions of Example I are duplicated except that the curing temperature of the PVA/PAA membrane is varied.

EXAMPLES VII-IX

In this series of examples, the conditions of Example I are duplicated except that the separating layer is prepared from polymers of different molecular weight.

The following Table sets forth (i) the weight ratio of PVA/PAA, (ii) the molecular weight of the PVA/PAA (x 1000), (iii) the curing temperature °C., (iv) the concentration w % of DMC in the feed, (v) the concentration w % of DMC in the Permeate, (vi) the Separation Factor, and (vii) the Flux (kmh).

From the above Table, the following conclusions may be drawn:

(i) Best Separation Factor is attained in Example I using a 50/50 membrane (cured at 150° C.) of PVA of $\overline{M}_n$ of 115,000 and PAA of $\overline{M}_n$ of 250,000;

(ii) Best Flux is attained in Example VIII using a 50/50 membrane (cured at 150° C.) of PVA of $\overline{M}_n$ of 96,000 and PAA of $\overline{M}_n$ of 90,000;

(iii) As the curing temperature rises from 110° C.–150° C., the Separation improves and highest flux is attained by use of membranes cured at higher temperature;

(iv) At constant molecular weight of 96,000 of PVA, better Separation and Flux are attained using PAA of lower molecular weight; and (v) At constant molecular weight of 115,000 of PVA, best Separation is attained using PAA of higher molecular weight.

Although this invention has been illustrated by reference to specific embodiments, it will be apparent to those skilled in the art that various charges and modifications may be made which clearly fall within the scope of the invention.

We claim:

1. The method comprising: treating a charge composition containing (i) an alcohol containing less than three carbon atoms and (ii) an oxygenate selected from the group consisting of organic ethers, aldehydes, ketones, and esters by a pervaporation process including, maintaining a non-porous membrane separating layer of a blend of a polyvinyl alcohol and a polyacrylic acid on a polyacrylonitrile support layer;

maintaining a pressure drop across said non-porous separating layer;

passing a charge composition containing (i) an alcohol having less than three carbon atoms and (ii) an oxygenate selected from the group consisting of organic ethers, aldehyde, ketones, and esters into contact with the high pressure side of said non-porous separating layer whereby at least a portion of said alcohol in said charge composition and a lesser portion of oxygenate pass by pervaporation through said non-porous separating layer as a lean mixture containing more alcohol and less oxygenate than are present in said charge composition and said charge composition is converted to a rich liquid containing less alcohol and more oxygenate than are present in said charge composition;

recovering as permeate from the low pressure side of said non-porous separating layer said lean mixture containing more alcohol and less oxygenate than are present in said charge composition, said lean mixture being recovered in vapor phase at a pressure below the vapor pressure thereof; and recovering as retentate from the high pressure side of said non-porous separating layer said rich liquid containing a lower alcohol content and a higher oxygenate content than are present in said charge composition.

2. The method claimed in claim 1 wherein the polyacrylonitrile support layer has a molecular weight cut-off of about 20,000–40,000.

3. The method claimed in claim 1 wherein the polyvinyl alcohol of the separating layer has a molecular weight $\overline{M}_n$ of about 96,000–115,000.

4. The method claimed in claim 1 wherein the polyacrylic acid of the separating layer has a molecular weight $\overline{M}_n$ of about 90,000–250,000.

5. The method comprising: treating a charge composition containing (i) methanol and (ii) dimethyl carbonate by a pervaporation process including, maintaining a non-porous membrane separating layer of a blend of a polyvinyl alcohol and a polyacrylic acid on a polyacrylonitrile support layer;

maintaining a pressure drop across said non-porous separating layer;

passing a charge composition containing methanol and dimethyl carbonate into contact with the high pressure side of said non-porous separating layer whereby at least a portion of said methanol in said charge composition and a lesser portion of dimethyl carbonate pass by pervaporation through said non-porous separating layer as a lean mixture containing more methanol and less dimethyl carbonate than are present in said charge composition and said charge composition is converted to a rich liquid containing less methanol and more dimethyl carbonate than are present in said charge composition;

recovering as permeate from the low pressure side of said non-porous separating layer said lean mixture containing more methanol and less dimethyl carbonate than are present in said charge composition, said lean mixture being recovered in vapor phase at a pressure below the vapor pressure thereof; and recovering as retentate from the high pressure side of said non-porous separating layer said rich liquid containing a lower methanol content and a higher dimethyl carbonate content than are present in said charge composition.

6. The method comprising: treating a charge composition containing (i) methanol and (ii) methyl t-butyl ether by a pervaporation process including, maintaining a non-porous membrane separating layer of a blend of a polyvinyl alcohol and a polyacrylic acid on a polyacrylonitrile support layer;

maintaining a pressure drop across said non-porous separating layer;

passing a charge composition containing methanol and methyl t-butyl ether into contact with the high pressure side of said non-porous separating layer whereby at least a portion of said methanol in said charge composition and a lesser portion of methyl t-butyl ether pass by pervaporation through said non-porous separating layer as a lean mixture containing more methanol and less methyl t-butyl ehter than are present in said charge composition and said charge composition is converted to a rich liquid containing less methanol and more methyl t-butyl ether than are present in said charge composition;

recovering as permeate from the low pressure side of said non-porous separating layer said lean mixture containing more methanol and less methyl t-butyl ether than are present in said charge composition, said lean mixture being recovered in vapor phase at a pressure below the vapor pressure thereof; and recovering as retentate from the high pressure side of said non-porous separating layer said rich liquid containing a lower methanol content and a higher methyl t-butyl ether content than are present in said charge composition.

* * * * *